(12) United States Patent
Meek et al.

(10) Patent No.: US 11,732,385 B2
(45) Date of Patent: Aug. 22, 2023

(54) EMULSION POLYMERIZATION OF NITRILES AND OTHER COMPOUNDS

(71) Applicants: Alliance for Sustainable Energy, LLC, Golden, CO (US); UT-Battelle, LLC, Oak Ridge, TN (US)

(72) Inventors: Kelly Marie Meek, Golden, CO (US); Todd R. Eaton, Denver, CO (US); Nicholas A. Rorrer, Golden, CO (US); Eric M. Karp, Denver, CO (US); Amit Kumar Naskar, Knoxville, TN (US)

(73) Assignees: Alliance for Sustainable Energy, LLC, Golden, CO (US); UT-Battelle, LLC, Oak Ridge, TN (US)

( * ) Notice: Subject to any disclaimer, the term of this patent is extended or adjusted under 35 U.S.C. 154(b) by 945 days.

(21) Appl. No.: 16/396,862

(22) Filed: Apr. 29, 2019

(65) Prior Publication Data
US 2019/0330400 A1    Oct. 31, 2019

Related U.S. Application Data

(60) Provisional application No. 62/664,383, filed on Apr. 30, 2018.

(51) Int. Cl.
| | |
|---|---|
| *C08F 220/44* | (2006.01) |
| *D01F 9/22* | (2006.01) |
| *C01B 32/05* | (2017.01) |
| *C08F 2/26* | (2006.01) |
| *C07C 253/22* | (2006.01) |
| *C07C 255/08* | (2006.01) |

(52) U.S. Cl.
CPC ............ *D01F 9/22* (2013.01); *C01B 32/05* (2017.08); *C07C 253/22* (2013.01); *C07C 255/08* (2013.01); *C08F 2/26* (2013.01); *C08F 220/44* (2013.01)

(58) Field of Classification Search
CPC ...... C08F 2/22; C08F 2/24; C08F 2/25; C08F 2/28; C08F 2/30; C08F 220/42; C08F 220/44; C08F 220/14; C08F 220/16; C08F 220/18; C08F 220/1802; C08F 220/1803; C07C 252/22; C07C 255/08
See application file for complete search history.

(56) References Cited

U.S. PATENT DOCUMENTS

| | | | | |
|---|---|---|---|---|
| 2,668,175 A | * | 2/1954 | Reppe | .............. C07C 253/22 |
| | | | | 558/311 |
| 4,179,462 A | | 12/1979 | Olivé et al. | |
| 4,935,180 A | * | 6/1990 | Daumit | ................ D01D 5/08 |
| | | | | 264/177.17 |
| 5,320,914 A | * | 6/1994 | Nakamura | ............ G11B 5/7023 |
| | | | | 428/424.4 |
| 2003/0055149 A1 | * | 3/2003 | McGee | ..................... C08F 2/28 |
| | | | | 428/424.4 |
| 2013/0313192 A1 | | 11/2013 | Wang et al. | |
| 2014/0330032 A1 | | 11/2014 | Lynch et al. | |
| 2014/0357880 A1 | | 12/2014 | Brandhorst et al. | |
| 2018/0346411 A1 | * | 12/2018 | Karp | ....................... B01J 21/08 |

FOREIGN PATENT DOCUMENTS

| | | |
|---|---|---|
| JP | 2893216 B2 | 5/1999 |
| WO | 2017/143124 A1 | 8/2017 |

OTHER PUBLICATIONS

Karp et al., "Renewable acrylonitrile production", Science, 2017, vol. 358, pp. 1307-1310.
Meek et al., "Emulsion polymerization of acrylonitrile in aqueous methanol", Green Chemistry, 2018, vol. 20, pp. 5299-5310.
Morris et al., "Synthesis, spinning, and properties of very high molecular weight poly(acrylonitrile-co-methyl acrylate) for high performance precursors for carbon fiber", Polymer, 2014, vol. 55, pp. 6471-6482.
Morris et al., "High performance carbon fibers from very high molecular weight polyacrylonitrile precursors", Carbon, 2016, vol. 101, pp. 245-252.
International Search Report and Written Opinion for International (PCT) Application PCT/US17/18272, dated Apr. 25, 2017, pp. 1-9.

\* cited by examiner

*Primary Examiner* — Robert C Boyle
(74) *Attorney, Agent, or Firm* — Michael A. McIntyre

(57) ABSTRACT

The present disclosure relates to a method that includes polymerizing a nitrile with an acrylate ester to form a copolymer, in a mixture that includes water and an alcohol ($R_2$—OH), according to the following reaction

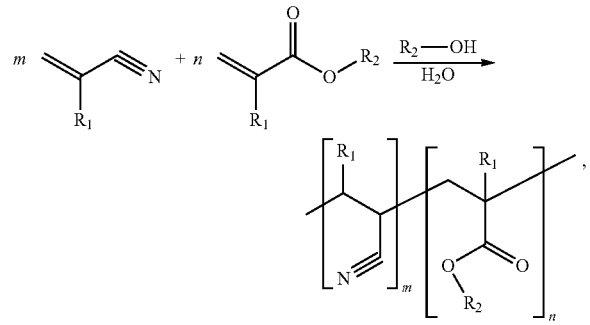

where $R_1$ includes at least one of a first aliphatic group or hydrogen, $R_2$ comprises at least one of a second aliphatic group or hydrogen, $100 \leq m \leq 4000$, and $1 \leq n \leq 4000$. In some embodiments of the present disclosure, the mixture may be an emulsion.

12 Claims, 8 Drawing Sheets

EMULSION POLYMERIZATION OF NITRILES AND OTHER COMPOUNDS

CROSS-REFERENCE TO RELATED APPLICATIONS

This application claims the benefit of U.S. Provisional Patent Application No. 62/664,383 filed Apr. 30, 2018, the contents of which are incorporated herein by reference in their entirety.

CONTRACTUAL ORIGIN

The United States Government has rights in this disclosure under Contract No. DE-AC36-08GO028308 between the United States Department of Energy and Alliance for Sustainable Energy, LLC, the Manager and Operator of the National Renewable Energy Laboratory. The United States Government has rights in this invention pursuant to contract no. DE-AC05-00OR22725 between the United States Department of Energy and UT-Battelle, LLC.

BACKGROUND

Carbon fiber (CF) is a high-performance material of increasing importance for designing lightweight, strong materials. CFs contain at least 90% carbon obtained by controlled pyrolysis of appropriate fiber precursors and have high tensile strengths (up to 7 GPa), excellent creep resistance, low densities, and high thermal and chemical resistance in the absence of oxidizers. These ideal material properties make CF attractive for use in composites as continuous or chopped fibers or as woven textiles. The CF sector is projected to grow substantially, with an expected annual increase of 11-18%, driven by the need to make automotive vehicles more fuel efficient by reducing their weights, as improved fuel economy offers significant potential for reducing greenhouse gas emissions and mitigating the harmful effects of global climate change.

The greatest obstacle for CF technology is the high precursor cost, and polyacrylonitrile (PAN) is the most widely utilized precursor in the market. Acrylonitrile (AN) is commercially produced via propylene ammoxidation, a technology originally developed in the 1950s by the SOHIO company. Although AN product yields have improved significantly since the 1950s, the chemistry produces significant quantities of hydrogen cyanide, acetonitrile, and acrolein, coproducts that require use of five separation columns to yield polymerization-grade AN. Propane ammoxidation as a route to AN has also garnered interest, because propane is cheaper and potentially of lesser environmental impact relative to propylene. Still, the volatility of petroleum, propylene, and propane prices leads to volatility in the AN market, presenting a significant problem for CF manufacturers, as approximately 50% of the cost of CF is due to AN costs.

Due to apprehension concerning propylene price volatility and environmental safety and sustainability issues, there remains a need to develop cost-effective, renewable, environmentally routes for synthesizing industrially relevant polymers to produce, among other things, CF.

SUMMARY

An aspect of the present disclosure is a method that includes polymerizing a nitrile with an acrylate ester to form a copolymer, in a mixture that includes water and an alcohol ($R_2$—OH), according to the following reaction

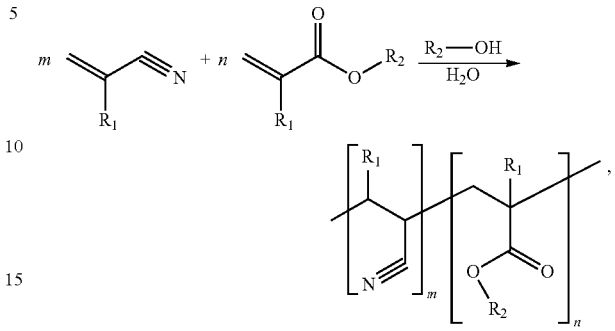

where $R_1$ includes at least one of a first aliphatic group and/or hydrogen, $R_2$ includes at least one of a second aliphatic group and/or hydrogen, $100 \leq m \leq 4000$, and $1 \leq n \leq 4000$. In some embodiments of the present disclosure, the mixture may be an emulsion.

In some embodiments of the present disclosure, the acrylate ester may include methyl acrylate, the nitrile may include acrylonitrile, and the copolymer may include

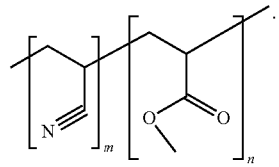

In some embodiments of the present disclosure, the copolymer may include at least one of polyacrylonitrile-random-polyacrylate, polyacrylonitrile-random-polymethylmethacrylate, polyacrylonitrile-random-polyethylacrylate, polyacrylonitrile-random-polyethylmethacrylate, polymethacrylonitrile-random-polyacrylate, polymethacrylonitrile-random-polymethylmethacrylate, polymethacrylonitrile-random-polyethylacrylate, and/or polymethacrylonitrile-random-polyethylmethacrylate. In some embodiments of the present disclosure, the copolymer may have a molecular weight between about 10 kDa and about 2000 kDa. In some embodiments of the present disclosure, the mixture may further include a surfactant. In some embodiments of the present disclosure, the mixture may further include a chain transfer agent (CTA).

In some embodiments of the present disclosure, the copolymer may have a peak temperature between about 200° C. and about 400° C., as determined by differential scanning calorimetry. In some embodiments of the present disclosure, the polymerizing may be performed at a temperature between about 25° C. and about 100° C. In some embodiments of the present disclosure, the copolymer may have an end group comprising at least one of an alkyl group or an alkoxy group. In some embodiments of the present disclosure, the method may further include converting the copolymer to a carbon fiber.

An aspect of the present disclosure is a composition that includes

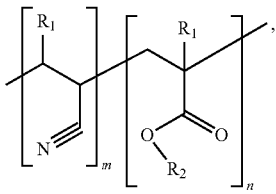

where $R_1$ includes at least one of a first aliphatic group and/or hydrogen, $R_2$ includes at least one of a second aliphatic group and/or hydrogen, $100 \leq m \leq 4000$, and $1 \leq n \leq 4000$. In some embodiments of the present disclosure, $R_1$ may include between 1 and 30 carbon atoms. In some embodiments of the present disclosure, $R_1$ may include at least one of an alkyl group, an alkenyl group, and/or an alkynyl group. In some embodiments of the present disclosure, $R_2$ may include between 1 and 30 carbon atoms. In some embodiments of the present disclosure, $R_2$ may include at least one of an alkyl group, an alkenyl group, or an alkynyl group.

In some embodiments of the present disclosure, the composition may have the structure defined by

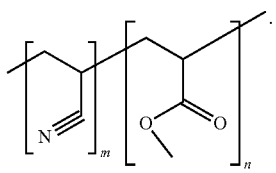

In some embodiments of the present disclosure, the composition may have a molecular weight between about 10 kDa and about 2000 kDa. In some embodiments of the present disclosure, the composition may have an end group that includes at least one of an alkyl group and/or an alkoxy group. In some embodiments of the present disclosure, the composition may have a peak temperature between about 200° C. and about 400° C., as determined by differential scanning calorimetry.

An aspect of the present disclosure is a composition having the structure

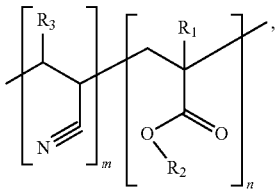

where $R_1$ includes at least one of a first aliphatic group and/or hydrogen, $R_2$ includes at least one of a second aliphatic group and/or hydrogen, $R_3$ includes at least one of a third aliphatic group and/or hydrogen, $100 \leq m \leq 4000$, and $1 \leq n \leq 4000$.

BRIEF DESCRIPTION OF THE DRAWINGS

Exemplary embodiments are illustrated in referenced figures of the drawings. It is intended that the embodiments and figures disclosed herein are to be considered illustrative rather than limiting.

REFERENCE NUMERALS

Figure 1:
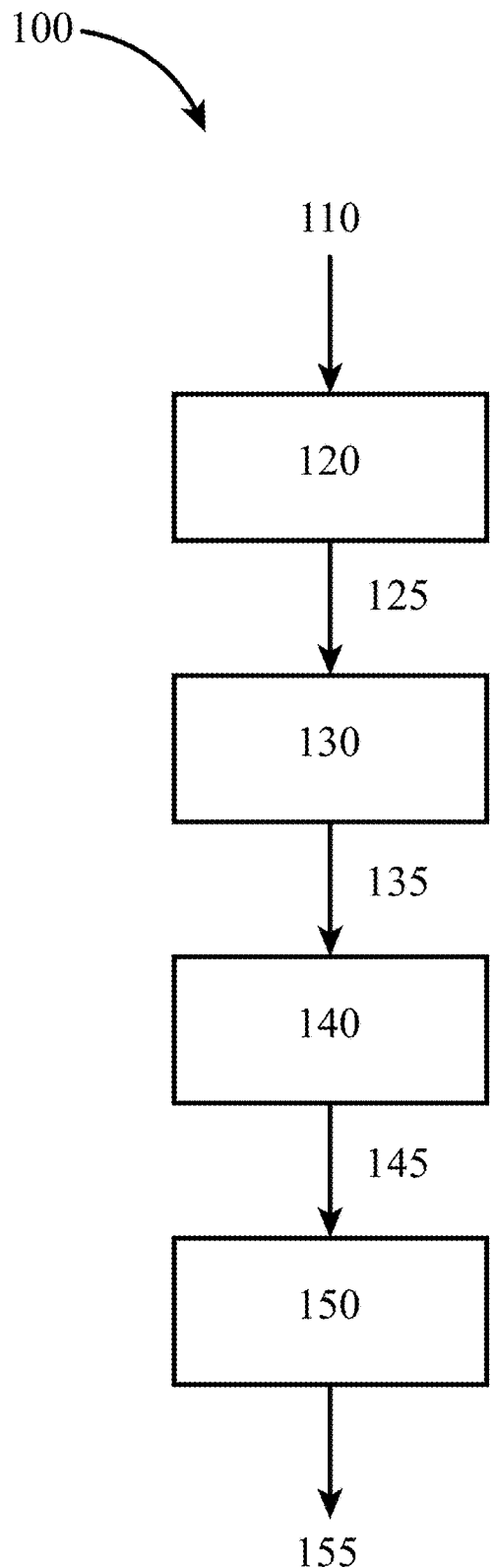
FIG. 1 illustrates a method for producing polymers, according to some embodiments of the present disclosure. Bioderived acrylonitrile is produced via nitrilation and polymerized in the presence of the reaction coproducts to yield a renewable carbon fiber precursor.

100 ... method
110 ... biomass
120 ... treating
125 ... acrylate ester
130 ... reacting
135 ... products and coproducts
140 ... polymerizing
145 ... copolymer
150 ... converting
155 ... carbon fiber

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Driven by the need for new, sustainable, cost-effective processes for bioderived AN, the quantitative conversion of acrylate esters was reported, which can be derived from 3-hydroxypropionic acid to acrylonitrile (AN) via catalytic nitrilation (see *Science*, Karp et al., 1307 (2017)). Specifically, a route was reported from ethyl 3-hydroxy-propanoate (ethyl 3-HP, derived from biologically-produced 3-hydroxypropionic acid, 3-HP) to AN at molar yields exceeding 90%. Methyl acrylate (MA) was directly obtainable from ethyl 3-HP through reactive distillation, which combined esterification, alcohol dehydration, and product separation into a single unit operation. In addition, a route from MA to AN via nitrilation was presented, at >90% yield. Using this nitrilation chemistry, depicted in Reaction 1 below, an acrylate ester was passed over a $TiO_2$ catalyst with excess ammonia at a temperature between 310° C. and 315° C., to produce stoichiometric amounts of AN, water, and alcohol (e.g., methanol for MA nitrilation) (see PCT Application Publication No. WO 2017/143124).

Reaction 1

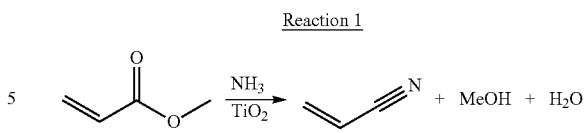

Nitrilation offers several advantages over other synthetic routes, which tend to be exothermic and inherently more hazardous and difficult to control. First, AN yields via nitrilation can exceed 98%. Additionally, Reaction 1 does not produce hazardous byproducts such as hydrogen cyanide (HCN), acetonitrile, and/or acrolein, which result in complicated downstream product separations and require expensive engineering procedures to insure safety. Instead, the nitrilation reaction byproducts, water and methanol (MeOH), are relatively simple and harmless molecules.

For at least these reasons, as described herein, nitrilation byproducts provide an ideal solvent basis for PAN synthesis, and/or other suitable nitrile-containing polymers and/or copolymers, via emulsion polymerization, effectively removing the need to purify AN after producing it. Thus, nitrilation of acrylate esters offers an efficient pathway to cost competitive, sustainable AN from renewably-sourced intermediates, and may also obviate the need for expensive, energy intensive distillation steps required for producing polymerization-grade AN, therefore overall significantly reducing both the cost and environmental impact of CF manufacturing.

Reaction 2 illustrates the generalized form of the nitrilation of an acrylate ester by reaction with ammonia, with an alcohol and water as coproducts:

Reaction 2

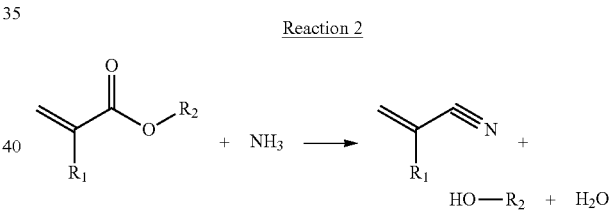

where $R_1$ and $R_2$ may be any suitable functional group. As used herein, the term "functional group" refers to any relatively small group of atoms covalently attached to a monomer, dimer, prepolymer, and/or polymer structure. For example, a functional group may be an aliphatic group and/or hydrogen. As used herein, an "aliphatic group" denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. A functional group may be an oxygenate, where the term "oxygenate" refers to any aliphatic group containing the element oxygen. In some embodiments of the present disclosure, a functional group may contain other elements, including at least one of nitrogen, sulfur, phosphorus, and/or a halogen.

In some embodiments of the present disclosure, the acrylate ester of Reaction 2 may be polymerized by emulsion polymerization, with the acrylate ester at least partially insoluble in the water and the alcohol, to produce a polymer, as shown in Reaction 3 below.

Reaction 3

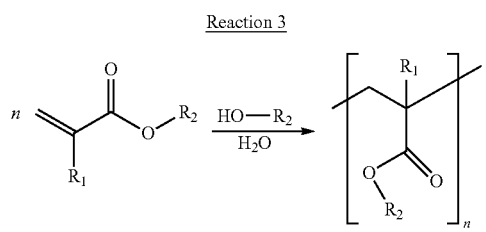

The acrylate ester may be unreacted acrylate ester from Reaction 2 and/or freshly supplied acrylate ester from a different source.

In some embodiments of the present disclosure, the nitrile produced in Reaction 2 may be copolymerized by emulsion polymerization with unreacted acrylate ester from Reaction 2 and/or acrylate ester from a different source to produce a copolymer, as shown in Reaction 4 below.

Reaction 4

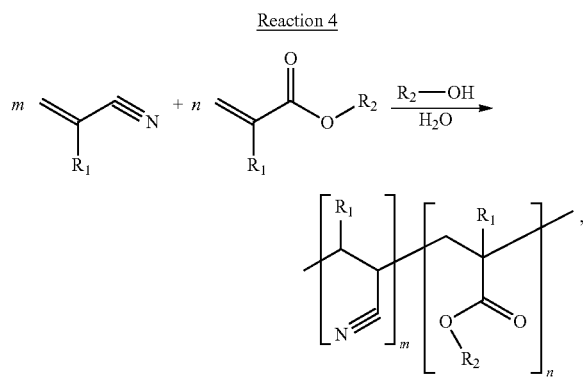

As shown herein, Reaction 4 has been demonstrated to produce a copolymer where $R_1$ is hydrogen, and $R_2$ is a methyl group. Specifically, acrylonitrile was reacted with methyl acrylate to produce polyacrylonitrile-random-polymethylacrylate copolymers (PAN-r-PMA). This is summarized in Reaction 5 below.

Reaction 5

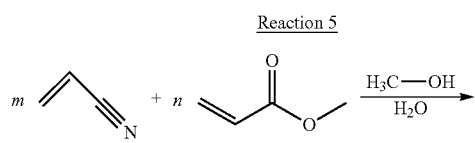

-continued

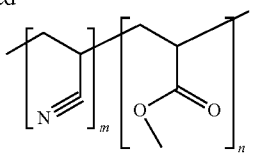

Other copolymers that may be produced according to Reaction 4 include polyacrylonitrile-random-polyacrylate, polyacrylonitrile-random-polymethylmethacrylate, polyacrylonitrile-random-polyethylacrylate, polyacrylonitrile-random-polyethylmethacrylate, polymethacrylonitrile-random-polyacrylate, polymethacrylonitrile-random-polymethylmethacrylate, polymethacrylonitrile-random-polyethylacrylate, and/or polymethacrylonitrile-random-polyethylmethacrylate.

The functional group, $R_1$, shown in Reactions 3 and 4 is for the example where the same acrylate ester being converted to a nitrile is the same acrylate ester that is copolymerized with the resultant nitrile. However, referring again to Reaction 4, in some embodiments of the present reaction, the $R_1$ functional group of the acrylate ester, may be the same and/or different than the $R_1$ functional group of the nitrile. In addition, both $R_1$ groups of Reaction 4 may include one or more different functional groups. Thus, in some embodiments of the present disclosure, the product of Reaction 4 may be a polymer that includes only two repeat units, and in some embodiments of the present disclosure, the polymer may include two or more repeat units. In other words. Similarly, each functional group of the polymer product of Reaction 4, both $R_1$ and $R_2$ for the acrylate ester repeat unit and $R_1$ for the nitrile repeat unit may be the same functional group or a mixture of two or more functional groups.

In some embodiments of the present disclosure, for Reaction 4 and/or Reaction 5, the resultant copolymer may include a nitrile-containing repeat unit where m is between about 100 and about 4,000. In some embodiments of the present disclosure, for Reaction 4 and/or Reaction 5, the resultant copolymer may include a methyl acrylate repeat unit where n is between about 1 and about 4,000, or between about 100 and about 1,000. In some embodiments of the present disclosure, m/(m+n) may be between about 0.02 and about 1.0, or between about 0.5 and about 1.0. In some embodiments of the present disclosure the resultant, the copolymer resulting from either Reaction 4 and/or Reaction 5 may have a molecular weight between about 10 kDa and about 2000 kDa, or between about 30 KDa and about 800 kDa.

FIG. 1 illustrates a method 100 proposed in this work whereby a bioderived nitrile is produced via nitrilation and polymerized, without further purification, in the presence of reaction coproducts (e.g. at least one of unreacted acrylate ester, an alcohol, and/or water, as shown in Reactions 4 and 5), to yield a nitrile-containing and acrylate ester-containing copolymer having molecular weights and material properties suitable for use as a precursor for producing high performance CF materials. In this example, the method 100 may begin with the treating 120 of biomass 110 to produce, among other things, at least one acrylate ester 125. In some embodiments of the present disclosure, the treating 120 may include at least one of chemical treating, heat treating, and/or biological treating. For example, chemical treating may include acid treating and/or alkaline treating. Heat treating may include heating the biomass to elevated temperatures in the presence and/or absence of oxygen. Biological treating may include contacting the biomass 110 with a native and/or engineered microorganism. Any one of these methods may result in the biomass 110 being deconstructed and/or depolymerized to produce an acrylate ester 125. The treating 120 may include one or more unit operations, as determined by the type of biomass 110 used as the starting raw material, the methods used for deconstructing the biomass 110, and the type and number of separation steps necessary to produce a relatively pure acrylate ester 125.

Regardless of the specifics of the treating 120, the resultant acrylate ester 125 may proceed to a reacting 130 step, where at least a portion of the acrylate ester 125 is converted to products and coproducts 135 by reacting with ammonia (not shown), according to Reactions 1 and 2 above. Referring to these reactions, at least a portion of the acrylate ester 125 may be converted to a nitrile-containing monomer (product), an alcohol, and/or water (coproducts). The products and coproducts 135, including a mixture of at least the nitrile-containing monomer, unreacted and/or freshly added acrylate ester 125, an alcohol and/or water may then proceed to a polymerizing 140 step, resulting in a copolymer 145 that includes nitrile-containing repeat units and acrylate ester-containing repeat units, as shown herein. A typical emulsion polymerization includes free-radical polymerizable monomers, a dispersion medium such as water, a surfactant, an initiator, and a CTA. The CTA is used to control the molecular weight and polydispersity of the final polymer by end-capping, or terminating, chains. In addition to dodecyl mercaptan or methanol, other CTAs could include ethanol, isopropyl alcohol, n-butyl mercaptan, n-decyl mercaptan. Reaction conditions may vary, such as reaction temperatures between about 40° C. and about 65° C. and/or reaction times between about 4 hours and 48 hours.

The copolymer 145 resulting from the polymerizing 140 may then proceed to a converting 150 step to produce carbon fiber 155. The copolymer 145 is finely milled and dissolved in solution at 8-20 wt % in an appropriate solvent, typically a polar aprotic such as DMF or DMSO. This solution, commonly referred to as a dope, is fiber spun into filaments using a wet-spinning line, and subsequently stretched and washed along a series of water/solvent baths. The resulting fibers may then be stabilized by heating in air at a temperature between about 200° C. and about 300° C. for a period of time between about 1 hour and about 2 hours. Finally, to carbonize fibers, they may be heated to a temperature between about 1000° C. and about 3000° C. in an oxygen-free furnace for about 30 minutes.

As described herein, AN produced via nitrilation can be polymerized directly in its reaction coproducts (e.g. alcohols and/or water), with no further separation, to produce polymers, demonstrating significant advantages over the incumbent methods for producing PAN. To demonstrate direct polymerization of AN obtained from nitrilation (without separating the monomer from coproduct solvent mixture), ten PAN-r-PMA based copolymers were synthesized using commercial AN: one with neither a chain transfer agent (CTA) nor MeOH, five with increasing levels of MeOH to act as a replacement CTA, and four with increasing levels of dodecyl mercaptan (DDM) CTA. The chemical structure, molecular weight, and thermal properties of these copolymers were evaluated for their suitability as CF precursors.

These results show that AN can be successfully copolymerized with MA without separation from MeOH and water, to produce controlled, high molecular weight copolymers. PAN-r-PMA copolymers synthesized in aqueous MeOH demonstrated thermal properties and carbon mass yields comparable to PAN copolymers prepared via conventional emulsion polymerization, suggesting optimal CF precursor properties. Experimental product flowrates with time-on-stream data are also described herein, demonstrating the stoichiometric production of AN, MeOH, and water during MA nitrilation, to determine the actual ratio of AN and byproducts produced, and to establish there are no additional byproducts produced from side reactions.

Figure 2:
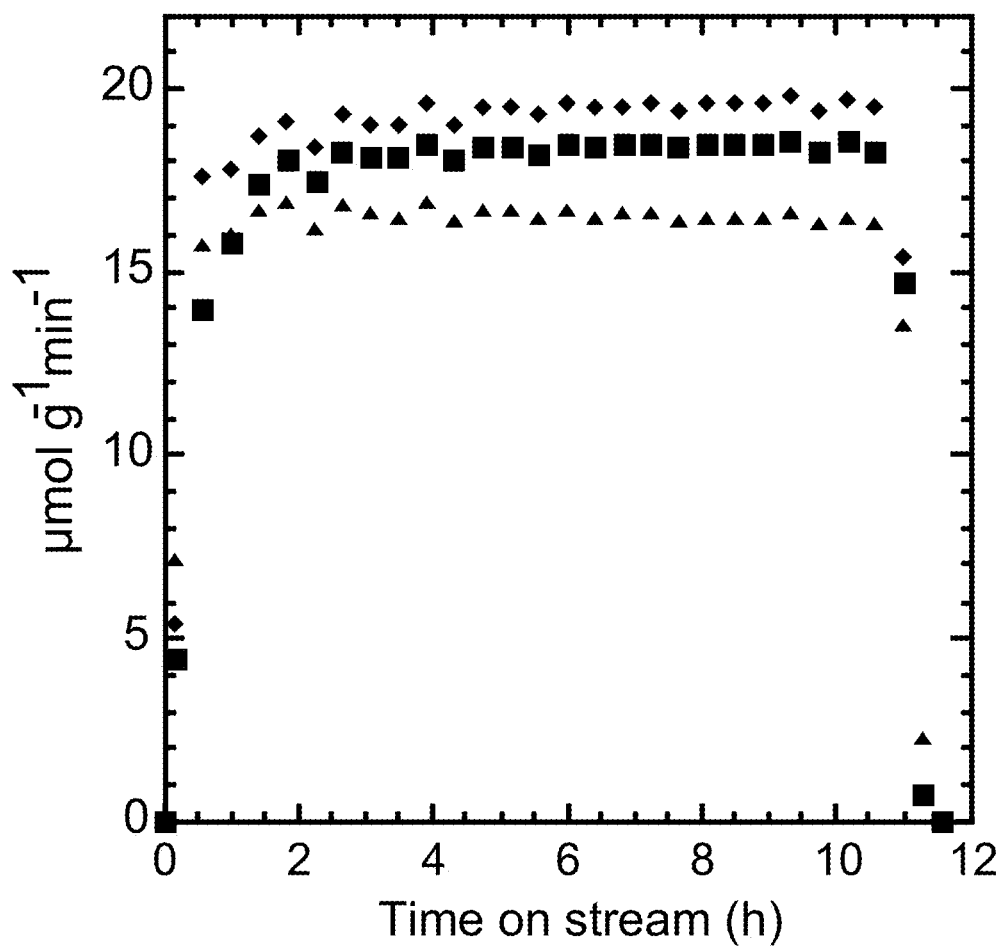
FIG. 2 illustrates product flowrates as a function of time-on-stream for methyl acrylate nitrilation over $TiO_2$, according to some embodiments of the present disclosure. Legend: acrylonitrile (squares), methanol (diamonds), and water (triangles). Conditions: 45 g $TiO_2$, 315° C., 1923 sccm $N_2$, 128 sccm $NH_3$, 0.077 mL min$^{-1}$ methyl acrylate. Acrylonitrile flowrate was equivalent to 97% between t=1 and 10.6 hours.

Using the "nitrilation" chemistry of Reaction 1 above, AN was produced by passing MA over a $TiO_2$ catalyst with excess ammonia at 310-315° C. to quantitatively produce stoichiometric yields of AN, water, and MeOH. Experimental product (AN) flowrates with time-on-stream are shown in FIG. 2. AN yield is 97%±3% between 1 hour and 10.6 hours on stream. The total amount of product generated can be calculated by integrating product flowrates from FIG. 2, giving total amounts of 0.52 mol AN (27.8 g), 0.56 moles MeOH (17.9 g), and 0.48 moles water (8.7 g).

Next, as described herein, the resultant AN was polymerized by aqueous emulsion polymerization in the presence of MeOH to produce PAN, thus foregoing the typical mercaptan-based CTA, and allowing MeOH to control the reaction instead. Herein, AN was polymerized via emulsion polymerization with varying concentrations of MeOH or DDM as CTA. In all runs, the amount of the surfactant (alkyldiphenyloxide disulfonate; DOWFAX™ 8390) remained constant. Surfactants are used in emulsion polymerization to lower the surface tension between the solution and the nitrogen environment, as well as to lower the interfacial tension between the water and the immiscible vinyl monomers. This allows for the emulsification of the reactive vinyl monomers and the subsequent formation of stable colloidal dispersions of nanosized polymer particles. There are numerous options for surfactants which will aid in the emulsification of nitrile- and acrylate-based monomers, stabilize the polymer particles during nucleation/growth, and maintain the stability of the resulting latex: Disponil SDS P, POLYSTEP A-15 F, Triton X-100, sodium lauryl sulfate.

Table 1 shows the resultant metrics of the PAN-r-PMA copolymers synthesized with no CTA (Sample 1), MeOH CTA (Samples 2-6), or DDM CTA (Samples 7-10). When no CTA (Sample 1) or minimal MeOH (Sample 2) was used, the product yield was sufficiently high, but the MN was less controlled. Sample 3, which used slightly more than equimolar MeOH to AN, was readily accessible by addition of slight excess of MeOH to the expected composition of AN and MeOH resulting from nitrilation reactions (see FIG. 2) and was successful in yielding a suitable copolymer for CF precursor. Sample 3 exhibited high MN, low polydispersity index (PDI), and unimodal distribution, such that the methyl acrylate nitrilation products herein are at a suitable composition for direct copolymerization of AN in its coproducts, MA, alcohol, and/or water, to yield a high quality copolymer suitable for use as a CF precursor. Samples 4-6 were obtained post-nitrilation by excess MeOH addition, allowing for facile targeting of desired molecular weights.

TABLE 1

Summary of PAN-r-PMA synthesized with various CTAs and CTA concentrations.

| Sample | Mol fed AN:MeOH | MeOH (CTA) (M) | DDM (CTA) (M × 10$^{-3}$) | Yield (wt %) | AN:MA (mol %)$^a$ | $M_N$ (kDa) | PDI |
|---|---|---|---|---|---|---|---|
| 1 | 1.00:0.00 | 0 | 0 | 92.9 | 97:3 | 726.3$^b$ | 13.3$^b$ |
| 2 | 1.00:0.58 | 2.3 | 0 | 79.7 | 97:3 | 507.7$^b$ | 13.5$^b$ |
| 3$^c$ | 1.00:1.14 | 4.6 | 0 | 79.5 | 97:3 | 331.7 | 1.875 |
| 4 | 1.00:2.29 | 9.3 | 0 | 63.9 | 97:3 | 226.3 | 2.074 |
| 5 | 1.00:3.44 | 13.7 | 0 | 34.9 | 97:3 | 82.5 | 2.097 |
| 6 | 1.00:4.46 | 17.7 | 0 | 21.0 | 97:3 | 50.4 | 1.987 |
| 7 | 1.00:0.00 | 0 | 2.5 | 88.6 | 96:4 | 150.9 | 2.288 |
| 8 | 1.00:0.00 | 0 | 5.0 | 90.8 | 97:3 | 117.5 | 2.465 |
| 9 | 1.00:0.00 | 0 | 10.0 | 88.6 | 96:4 | 85.8 | 2.843 |
| 10 | 1.00:0.00 | 0 | 15.1 | 94.3 | 97:3 | 38.9 | 2.279 |

$^a$Molar composition of polymer as determined by $^1$H NMR spectroscopy. All reactions were fed a ratio of 97 moles AN:3 moles MA and reacted for 24 h at 65° C.
$^b$An additional lower molecular weight shoulder peak was detected in the SEC chromatogram. The higher molecular weight peak is reported here; molecular weight analysis of the lower molecular weight peak is provided in Table S1. The PDI reported here is representative of the overall $M_N$, including the lower molecular weight peak.
$^c$Sample 3 composition is readily accessible directly from the product mixture resulting from nitrilation of MA.

Figure 3:
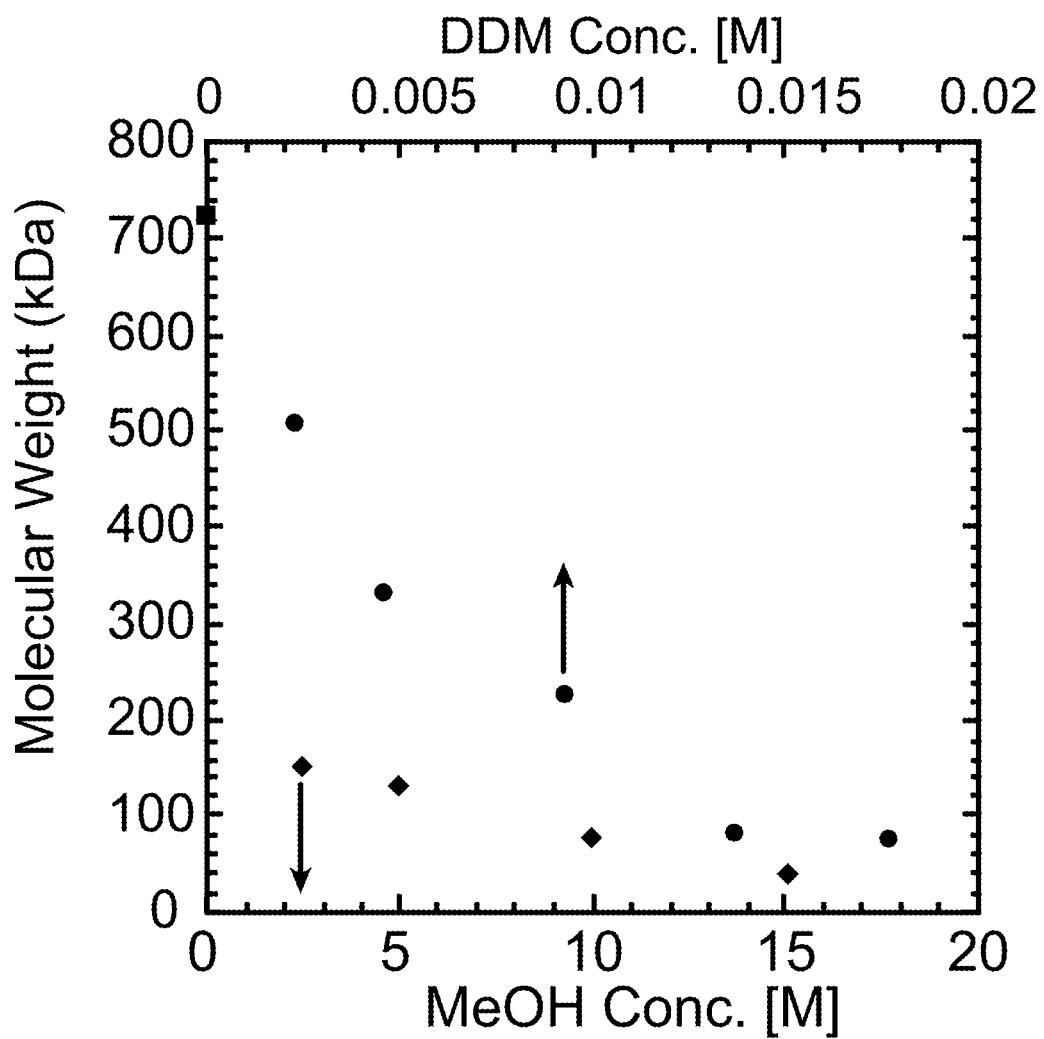
FIG. 3 illustrates the molecular weights of random polyacrylonitrile-random-polymethylacrylate copolymers (abbreviated herein as PAN-r-PMA) as a function of (circles) MeOH CTA concentration and (diamonds) dodecyl mercaptan (DDM) CTA concentration, according to some embodiments of the present disclosure.

FIG. 3 compares the molecular weights of copolymers as a function of the concentration of MeOH (data set with circles as markers) or DDM (diamonds) CTA used. As expected, because of the lower chain transfer constant of MeOH, a significantly higher concentration of MeOH was used to control the molecular weight distribution than if DDM were used. At the bench-scale (50 g), the molecular weight region of >150 kDa was not easily accessible with DDM, because an exceedingly small amount of the liquid CTA (<50 mg) would have to be measured accurately. At industrial scale, DDM may be scaled to higher volumes that may make higher molecular weight copolymers more accessible. However, MeOH was shown to produce lower PDIs at similar MN (see Table 1, Sample 5 and Sample 9), which is highly desirable for CF precursor. Overall, these data demonstrate that MeOH provided a readily accessible, broad window of PAN molecular weight, and provided improved control over polydispersity.

Figure 4:
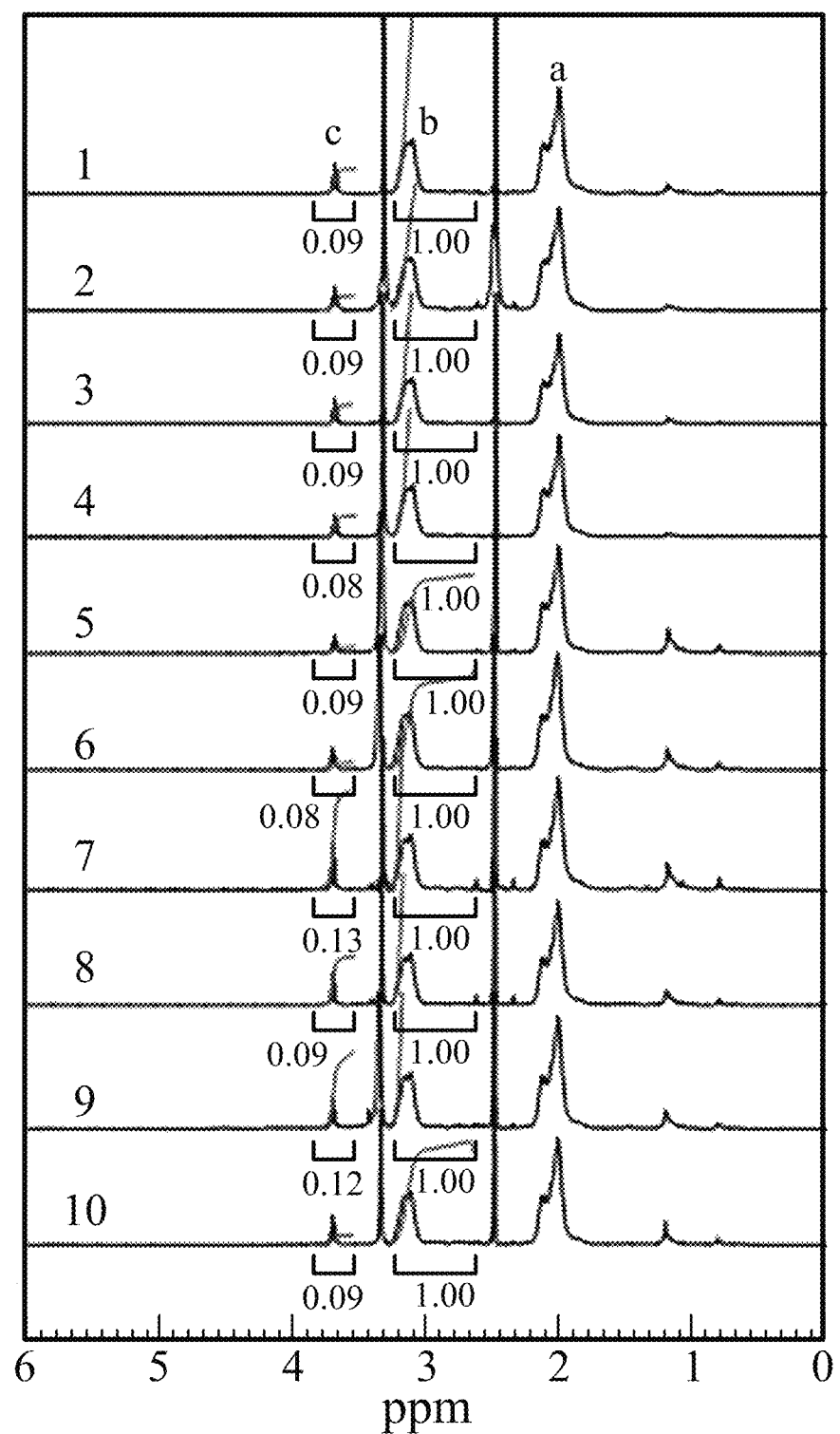
FIG. 4 illustrates $^1$H NMR spectra of PAN-r-PMA samples, according to some embodiments of the present disclosure.

The chemical structure, composition, and purity of the ten PAN-r-PMA copolymer samples was investigated by $^1$H NMR spectroscopy. FIG. 4 shows $^1$H NMR spectra of the ten samples. Copolymer molar compositions were determined by comparing the integral of the methine (CH) protons from PAN and PMA units at 3.2 ppm (b; integrated from 3.28 ppm to 2.66 ppm) to the integral of the methyl (CH$_3$) protons of the PMA units at 3.7 ppm (c; integrated from 3.80 ppm to 3.53 ppm), such that the molar ratio of MA in the copolymer was calculated from the integral values of the methyl protons relative to the methine protons (i.e., (c/3)/b). The acrylate co-monomer in the PAN precursor markedly influences the microstructure of resultant precursor fibers, with ~3 mol % MA incorporation being found suitable for precursor development, and increased MA interfering with cyclization. Because AN is the product of MA nitrilation, running at 97% nitrilation conversion would even allow use of the mixture directly without adding 3 mol % MA. All samples fall within this narrow range of ideal composition (3-4 mol % MA). As expected, end groups make up a greater proportion of the polymer composition (i.e., are more evident in $^1$H NMR at 1.3 to 0.8 ppm) in samples employing a dodecyl end group from DDM (Samples 7-10), and in samples with a lower degree of polymerization relative to the methoxyl end group from MeOH (Samples 5-6). In industrial PAN CF precursors, a small quantity (<1 mol %) of stabilization accelerant monomer (such as itaconic acid or acrylic acid) may also be included. We aimed to keep the composition as a copolymer, mimicking industrial textile PAN copolymer that has promise as CF precursors, but the chemistry presented herein could readily incorporate such an accelerant.

Figure 5A:
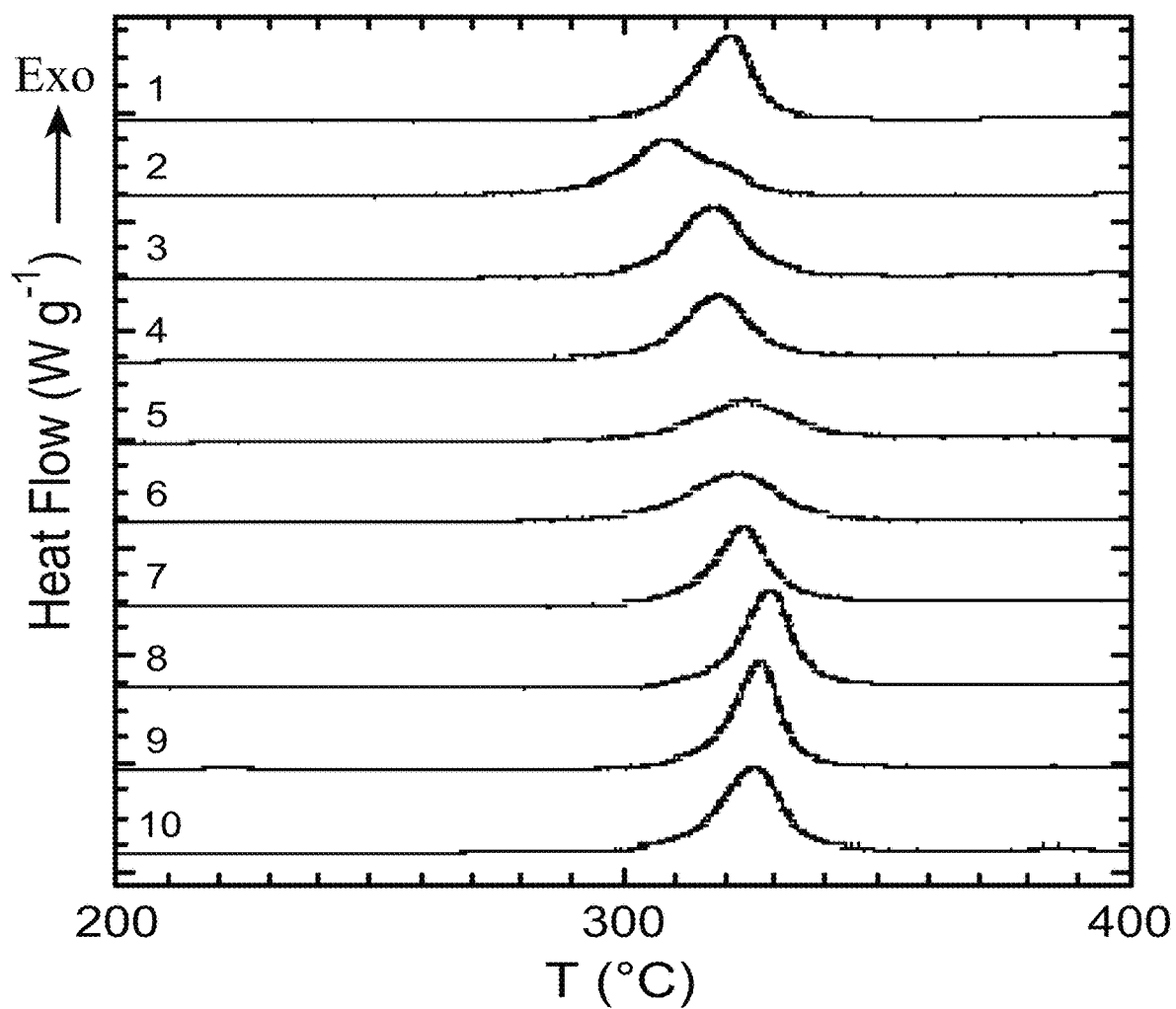
FIG. 5A illustrates differential scanning calorimetry analysis (DSC) of PAN-r-PMA samples, according to some embodiments of the present disclosure.

The effect of altering the PAN copolymer architectures and end groups on the thermal stabilization process was investigated by differential scanning calorimetry (DSC), thermal gravimetric analysis (TGA), and Fourier Transform infrared (FTIR) spectroscopy to evaluate the copolymers potential as CF precursors, relative to their preparation technique. The exothermic events evidenced by DSC analysis in FIG. 5A indicate cyclization reactions. Thermal characterization by DSC was performed under nitrogen at a ramp rate of 10° C./min to investigate the extent of thermal cyclization reactions. In contrast to PAN homopolymer cyclization, which is initiated in the amorphous phase through a radical mechanism yielding a sharp intense exotherm, PAN co-monomers exert a diluent effect such that the copolymer exotherms are broadened and have a lower energy peak release. PAN homopolymer exotherms typically have peak temperatures of 260-280° C. depending on heating rate, while increasing MA content in PAN copolymers results in an increase of exothermic peak temperatures. As defined herein, a copolymer's "peak temperature" is defined by testing the copolymer by DSC, as described herein, and identifying the maximum temperature of the copolymer's exotherm, as shown in the examples of FIG. 5A. All of the PAN copolymer samples exhibited relatively symmetric, narrow exotherms, with peak temperatures centered between 309° C. and 329° C. Peak temperatures and the corresponding maximum heat flows are listed in Table 2. The samples with thiol-based end groups (Samples 7-10) exhibited slightly higher peak temperatures relative to the samples with methoxyl-based end groups (Samples 2-6), indicating that end-group effects cannot be neglected. Samples with thiol-based end groups (Samples 7-10) also generally reached a higher peak heat flow. These differences can likely be attributed to the higher reactivity of thiol groups relative to methoxyl groups. All samples showed maximum heat flows of <10 W/g, which is an appropriately low amount of energy released over the narrow temperature range to avoid prematurely degrading the polymer backbone. Interestingly, Sample 2 had a notably lower peak cyclization temperature relative to all other samples. Thermal properties of the PAN copolymers were further investigated by TGA, shown in FIG. 5B. Final mass yields from TGA are summarized in Table 2. Mass loss post-cyclization is an indicator of carbon content, where greater mass retention suggests formation of a more complete ladder structure. TGA thermogram regions are as follows (see FIG. 5B):

(1) Cyclization: the exothermic cyclization reaction, which occurs during the plateau between 200 and 300° C., represents the formation of the aromatic ladder structure and should theoretically not include weight loss.

(2) Dehydration: rapid weight loss between 300 and 350° C. during the conversion of C—C bonds to C=C bonds due to the heat generated during cyclization, accompanied by release of small molecules such as water and carbon dioxide.

(3) Steady weight loss between 350 and 450° C. due to continued removal of small molecules from the cyclized ladder structure such as methane, ammonia, hydrogen cyanide, water, and carbon dioxide.

(4) Weight loss in the stabilized structure plateaus between 450 and 600° C.

(5) Carbonization: steady weight loss above 600° C. from release of hydrogen cyanide, ammonia, nitrogen, and hydrogen.

Figure 5B:
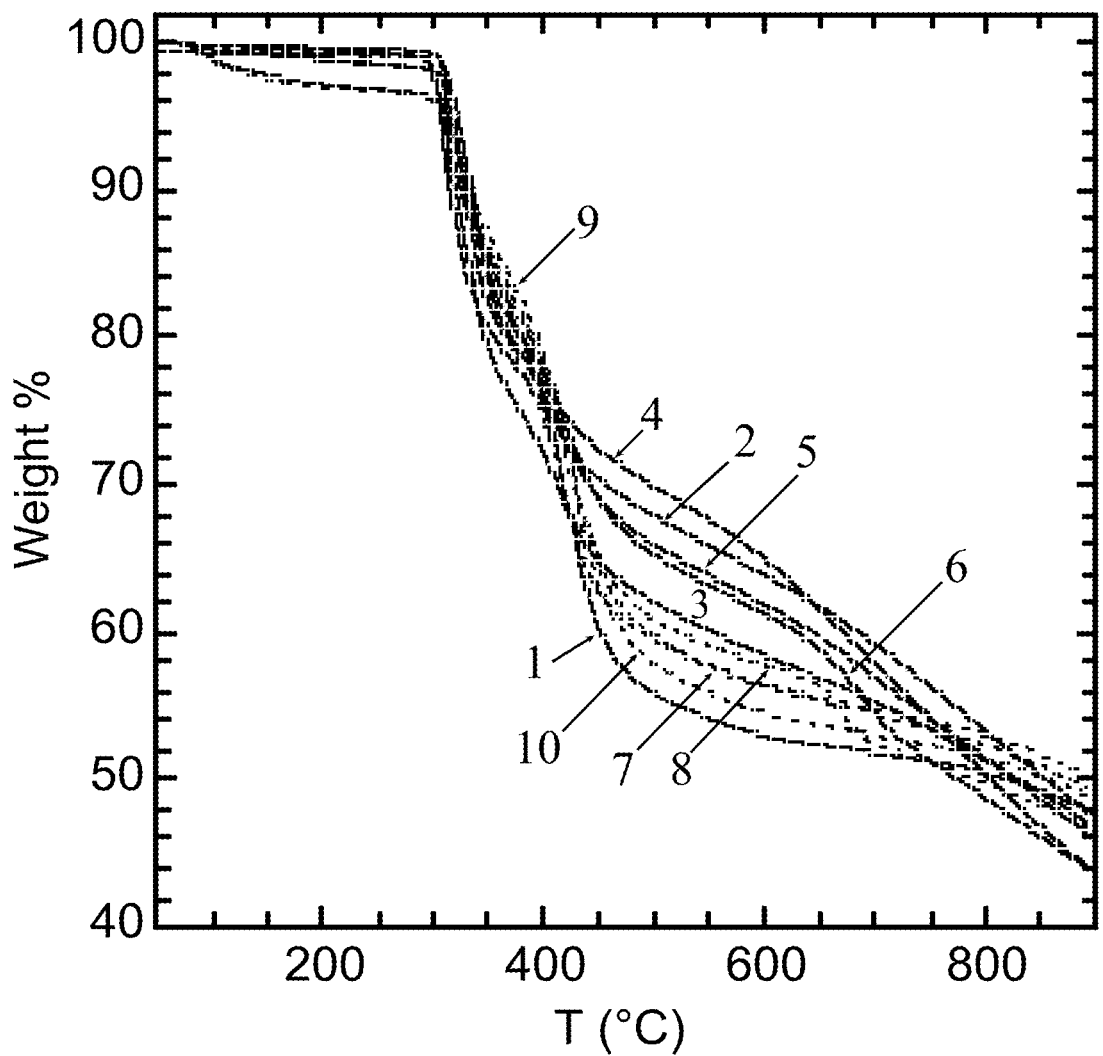
FIG. 5B illustrates thermal gravimetric analysis (TGA) of PAN-r-PMA samples, according to some embodiments of the present disclosure.

It is apparent in FIG. 5B that the mass loss for the methoxyl group end-capped polymers is not as steep between 300 and 400° C. as for those with thiol end groups. This is in agreement with the greater heat flow generated during cyclization observed in the DSC of Samples 7-10, which would cause more rapid mass loss. However, Samples 7-10 show more weight loss after 400° C. such that the final residual mass content for all samples at 900° C. falls within a range of 44-50 wt %, suggesting that end group and molecular weight effects are negligible in the overall goal of creating a ladder structure capable to withstand carbonization.

TABLE 2

Summary of PAN-r-PMA thermal properties.

| Sample | Peak Temperature (° C.)[a] | Heat Flow (W/g)[b] | Mass Yield (wt %)[c] |
|---|---|---|---|
| 1 | 321 | 5.6 | 47.8 |
| 2 | 309 | 4.1 | 47.8 |
| 3 | 317 | 5.0 | 47.1 |
| 4 | 318 | 4.6 | 44.0 |
| 5 | 325 | 2.7 | 46.3 |
| 6 | 324 | 3.4 | 43.9 |
| 7 | 323 | 5.4 | 49.4 |
| 8 | 329 | 6.8 | 46.8 |
| 9 | 327 | 7.5 | 50.2 |
| 10 | 325 | 5.7 | 48.8 |

Figure 6A:
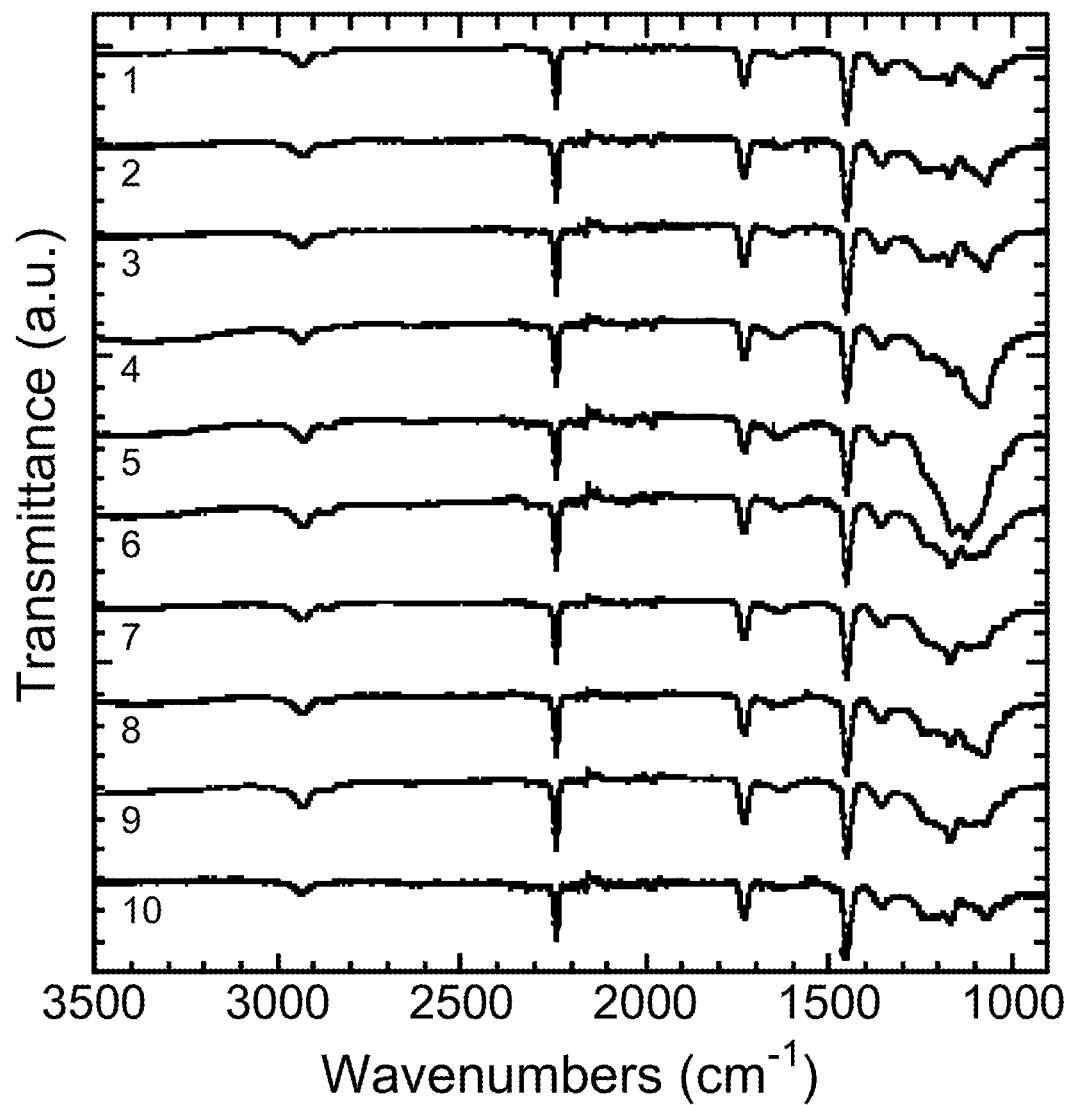
FIG. 6A illustrates FTIR spectra of PAN-r-PMA samples before heat treatment, according to some embodiments of the present disclosure.

[a]Temperature at maximum heat flow from DSC under $N_2$ at ramp rate of 10° C./min
[b]Maximum heat flow at peak temperature from DSC under $N_2$ at ramp rate of 10° C./min
[c]Final mass from TGA under $N_2$ at ramp rate of 10° C./min As cyclization and dehydrogenation reactions of CF precursor are essential steps in the successful conversion of precursor to graphitic carbon, the chemical structures of the ten samples were analyzed by FTIR spectroscopy prior to heat treatment and during the cyclization/dehydrogenation reactions, to determine their suitability as CF precursor and evaluate potential differences in thermal behavior arising from preparation method. FIG. 6A shows the FTIR spectra of untreated PAN-r-PMA samples and samples after being heated to 500° C. at 10° C./min under nitrogen with TGA.

The FTIR spectra of the pristine PAN-r-PMA samples exhibited characteristic peaks of the vibrations of nitrile groups (C≡N at 2243 $cm^{-1}$), a hydrocarbon backbone (C—H in $CH_2$ at 2940 $cm^{-1}$ and 1454 $cm^{-1}$, C—H in CH at 1360 $cm^{-1}$), and an ester group (C=O at 1732 $cm^{-1}$, C—O—C at 1171 $cm^{-1}$). The peak at 1073 $cm^{-1}$ is associated with the PAN fingerprint region, where assignment is uncertain. Minimal differences are noted between samples; all samples contain the major peaks associated with PAN and PMA (C≡N, C—H, C=O) in the expected relative ratios, with variation in the fingerprint region, likely associated with residual water or end groups.

Figure 6B:
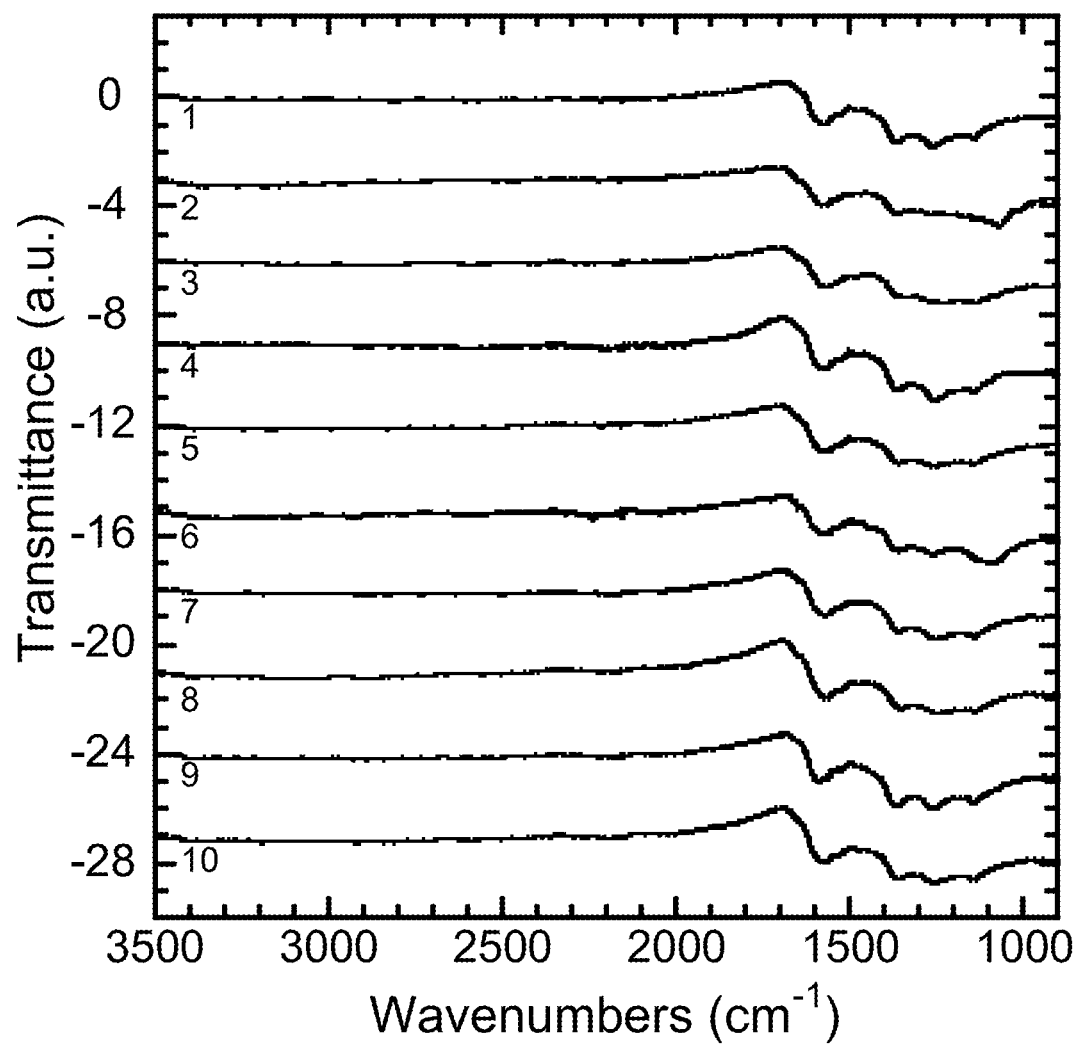
FIG. 6B illustrates FTIR spectra of PAN-r-PMA samples after heating to 500° C. by TGA, according to some embodiments of the present disclosure.

Evidence of cyclization can be clearly observed after heat treatment in FIG. 6B. The cyclization reaction converted —C≡N groups into cyclic —C=N— and —C—N— groups, as demonstrated by the disappearance of the nitrile peak at 2243 $cm^{-1}$. The peak at 1587 $cm^{-1}$ represents cyclic —C=C— and —C=N— groups and the peak at 1267 $cm^{-1}$ represents cyclic —C—N— group resulting from successful cyclization. Minimal difference is noted across samples, indicating negligible interference of end groups with cyclization. Table 3 summarizes the characteristic FTIR peak frequencies and functional groups of PAN before and after heat treatment.

TABLE 3

FTIR peaks of PAN-r-PMA before and after heat treatment.

| Before Heat Treatment | | After Heat Treatment | |
|---|---|---|---|
| Peak frequency ($cm^{-1}$) | Functional Group | Peak frequency ($cm^{-1}$) | Functional Group |
| 2940 | C—H | 1587 | C=C, C=N |
| 2243 | C≡N | 1370 | C—H |
| 1732 | C=O | 1267 | C—N, C—C |
| 1454 | C—H | — | — |
| 1360 | C—H | — | — |
| 1247 | C—O | — | — |
| 1171 | C—O—C | — | — |
| 1073 | Fingerprint | — | — |

As disclosed herein, new procedures to copolymerize nitrile-containing monomers (e.g. AN) and acrylate esters (e.g. MA) in the presence of water and alcohols (e.g. methanol) were developed for yielding renewable copolymers containing randomly dispersed nitrile-containing repeat units and acrylate ester-containing repeat units. This novel chemistry is particularly advantageous over ammoxidation, the current standard for producing AN; ammoxidation yields byproducts of hydrogen cyanide, acetonitrile, and acrolein which are toxic and detrimental to polymerization, and thus require expensive separations to acquire polymerization-grade AN. Additionally, direct polymerization and/or copolymerization of nitrilation products gives the option to recover the alcohol coproducts post-polymerization for subsequent industrial use. In a typical emulsion polymerization of acrylic monomers, DDM is the most commonly employed CTA, with a relatively high chain transfer constant. There is interest in substituting DDM with a more benign CTA, as it is toxic and exhibits a repulsive odor. Herein, we show that an alcohol (e.g. methanol) can replace DDM in the emulsion polymerization of AN at higher concentrations due to the lower chain transfer constant of MeOH As shown in the polymerization summary in Table 1, the yield for all of the samples employing MeOH as the CTA, ranged from 21.0 wt % to 79.7 wt % relative to experimental yields ranging from 88.6 wt % to 94.3 wt % for the samples employing DDM as the CTA. However, when MeOH is used as the CTA, one less separation step is required; to further separate pure AN from the ternary mixture would require azeotropic distillation, employing an entrainer. Preliminary results utilizing methyl acetate as an entrainer resulted in low yield (~54%) of relatively high purity (>95 wt %) AN, by spinning band distillation at atmospheric pressure. Although yield would arguably be higher in a continuous column at the industrial scale, at the laboratory scale this translates to a reduction in overall yield for Samples 7-10 by approximately a factor of two, making overall yields for Samples 2-4 more favorable.

Experimental product flowrates of MA nitrilation are shown in FIG. 2. Gas phase products are quantified using an FTIR continuous gas analyzer, to reveal near stoichiometric amounts of AN (0.52 mol), MeOH (0.56 mol), and water (0.48 mol). Trace water in the FTIR nitrogen purge gas (50-60 ppm) makes accurate quantification of water challenging, which explains the less-than-stoichiometric amount of water in the product stream. In addition to stabilization in temperatures up to 400° C. and carbonization in temperatures up to 1,600° C., CF precursor must be able to withstand graphitization in temperatures up to 3,000° C. Typically, efforts to enhance CF tensile strength have concentrated on the stabilization and carbonization reaction, emphasizing the importance of the thermal properties of the precursor. In this study, minor differences were observed in the DSC and TGA thermograms, according to how the copolymer was prepared. Typical carbon yields for CF precursors are ~50%, which was closely matched by Sample 3, at 48 wt % recovery. Ultimately, mass yields at 900° C. were comparable for PAN copolymers prepared in aqueous MeOH relative to water, and minimal weight loss is expected after 900° C., suggesting that the PAN copolymers would have suitable thermal properties for acting as CF precursor.

Whether or not a reactant or product described herein is "bioderived" may be determined by analytical methods. Using radio carbon and isotope ratio mass spectrometry analysis, the biobased content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pNMC value obtained correlates directly to the amount of biomass material present in the sample. Thus, ASTM-D866 may be used to validate that the compositions described herein are and/or are not derived from renewable sources.

Materials and Method:

Acrylonitrile (≥99%, contains 35-45 ppm monomethyl ether hydroquinone as inhibitor) and methyl acrylate (99%, contains ≤100 ppm monomethyl ether hydroquinone as inhibitor) were obtained from Sigma-Aldrich and passed through inhibitor removal columns packed with $Al_2O_3$. Methanol, ammonium persulfate, dodecyl mercaptan, and magnesium sulfate were used as received from Sigma-Aldrich. DOWFAX 8390 surfactant was obtained from The Dow Chemical Company. Deionized (DI) water was used as appropriate.

Polymer synthesis: Synthesis of copolymer PAN-r-PMA was performed by emulsion polymerization of commercially available acrylonitrile. Results of a typical polymerization using no chain-transfer agent (CTA) are listed in Table 1, Sample 1. The reaction mixture contained 175 mL water, 5.15 g surfactant (DOWFAX 8390), 51.25 g AN, 2.60 g MA, 34 mg initiator (ammonium persulfate). All materials were stirred in a round bottom flask and purged with nitrogen for 0.5 h, then reacted under nitrogen balloon at 65° C. for 24 h. The resultant emulsion was added to 700 mL of a 1 wt % aqueous $MgSO_4$ solution at 70° C. and stirred briefly to break the emulsion, then the solid polymer was filtered. The solid powder was washed by stirring in 500 mL of DI water, filtered, and dried at 70° C. under convection overnight. Yield 50.0 g of solid white powder (92.9%).

Results of typical emulsion polymerizations of PAN-r-PMA using MeOH as a CTA are listed in Table 1, Samples 2-6. In a typical reaction (Sample 3), the reaction mixture contained 130 mL water, 45 mL MeOH, 5.15 g surfactant (DOWFAX 8390), 51.25 g AN, 2.60 g MA, 34 mg initiator (ammonium persulfate). All materials were stirred in a round bottom flask and purged with nitrogen for 0.5 h, then reacted under nitrogen balloon at 65° C. for 24 h. The resultant emulsion was added to 700 mL of a 1 wt % aqueous $MgSO_4$ solution at 70° C. and stirred briefly to break the emulsion, then the solid polymer was filtered. The solid powder was washed by stirring in 500 mL of DI water, filtered, and dried at 70° C. under convection overnight. Yield 42.8 g of solid white powder (79.5%). Additional polymerizations following the same procedure were performed at various concentrations of MeOH to produce a range of molecular weights. MeOH volume was varied linearly, and water was added in corresponding volumes such that the total separate volumes of the MeOH and water totaled to 175 mL; note that because alcohol and water volumes are not additive, upon combining the solvents the volume decreased such that total solution volume across reactions varied slightly. Synthesis results are summarized in Table 1, Samples 2-6.

Results of typical emulsion polymerizations of PAN-r-PMA using DDM as a CTA are listed in Table 1, Samples 7-10. In a typical reaction (Sample 8), the reaction mixture contained 175 mL water, 5.15 g surfactant (DOWFAX 8390), 51.25 g AN, 2.60 g MA, 250 mg chain-transfer agent (dodecyl mercaptan (DDM)), 34 mg initiator (ammonium persulfate). All materials were stirred in a round bottom flask and purged with nitrogen for 0.5 h, then reacted under nitrogen balloon at 65° C. for 24 h. The resultant emulsion was added to 700 mL of a 1 wt % aqueous $MgSO_4$ solution at 70° C. and stirred briefly to break the emulsion, then the solid polymer was filtered. The solid powder was washed by stirring in 500 mL of DI water, filtered, and dried at 70° C. under convection overnight. Yield 48.9 g of solid white powder (90.8%). Additional polymerizations following the same procedure were performed at various concentrations of DDM to produce a range of molecular weights. Synthesis results are summarized in Table 1, Samples 7-10.

Molecular Weight Characterization: Molecular weight (MN) and molecular weight distribution (polydispersity index, PDI) were determined in DMF (with 0.05 mol LiBr) via size exclusion chromatography (SEC) at 60° C. and a flowrate of 1 mL min$^{-1}$. The SEC system consisted of a Waters 1515 Isocratic HPLC pump equipped with 2414 Refractive Index (RI) detector. Polyethylene oxide/polyethylene glycol standards were used with Styragel HR 3 and HR 4 columns maintained in a column heater compartment. Integration was performed against standards using Empower software. Eluograms were baseline corrected to zero at 8 min elution time and normalized by peak intensity. MN and PDI of the copolymers are listed in Table 1, and MN is plotted relative to CTA concentration in FIG. 3.

Thermal Characterization: Thermal behavior of the copolymers was observed by differential scanning calorimetry (DSC; TA Instruments, Q2000) over a temperature range of 0 to 450° C. at a heating/cooling rate of 10° C./min under a $N_2$ environment using a heat/cool/heat method. Thermal degradation of the copolymers was measured by thermal gravimetric analysis (TGA; TA Instruments, Q500) using a temperature ramp to 900° C. at a heating rate of 10° C./min under a $N_2$ environment. Intermediate cyclization products were also produced by TGA using a temperature ramp to 500° C. at a heating rate of 10° C./min under a $N_2$ environment. Thermograms resulting from DSC and TGA analysis are shown in FIGS. 5A and 5B, respectively.

Structural Characterization: Chemical structures and compositions of the copolymers and AN solution were characterized by $^1$H NMR spectroscopy (see FIG. 4) using a Varian 500 MHz spectrometer at 23° C. with DMSO-$d_6$ as the solvent. The chemical shifts were referenced to DMSO-$d_6$ at 2.50 ppm. Copolymer molar compositions were determined by comparing the integrals of the proton signals in the repeat units. The signal at 3.2 ppm (b; integrated from 3.28 ppm to 2.66 ppm) corresponds to the methine (CH) protons from PAN and PMA. The signal at 3.7 ppm (c; integrated from 3.80 ppm to 3.53 ppm) corresponds to the methyl ($CH_3$) protons of the PMA units. The molar content of MA in the copolymer was calculated from the integral values of the methyl protons relative to the methine protons (i.e., (c/3)/b). Chemical structures of the copolymers and intermediate cyclization products were investigated with infrared spectroscopy using a Fourier transform infrared (FTIR) spectrometer (PerkinElmer Frontier). All spectra were collected at 32 scans per spectrum. Before each experiment, a background spectrum was collected, and each subsequently collected spectra was subtracted from the background spectrum. FIGS. 6A and 6B show FTIR spectra for PAN-r-PMA and intermediate cyclization products. Table 2 provides a summary of the characteristic FTIR peak frequencies and functional groups of the PAN copolymers before and after heat treatment.

Methyl Acrylate Nitrilation: Nitrilation experiments were performed in a vapor-phase flow reactor system with heated lines and a 0.75" ID×8" long reactor (Parr Instrument Company). Gas was delivered with nitrogen and ammonia mass flow controllers (MKS instruments), and methyl acrylate was delivered with an NE-1000 (New Era Pump Systems Inc.) syringe pump, wherein methyl acrylate was injected into a heated nitrogen carrier stream. Ammonia was introduced just upstream of the reactor bed. The reactor bed was packed with catalyst held between two quartz plugs, with 1 mm, 2 mm, and 3 mm glass beads packed upstream of the catalyst bed to mix gases and prevent channeling. The effluent gas is quantified with an online MKS MultiGas 2030 FTIR continuous gas analyzer with a 2-cm cell (MKS Instruments) calibrated with authentic standards to quantify all reactant and product gases simultaneously. For the nitrilation of methyl acrylate the reactor was packed with 45 g of $TiO_2$ (Johnson-Matthey, 0.5 mm particle size, roughly 45 mL bed volume), and heated to 315° C. under flowing nitrogen (1923 sccm). Once the reactor reached the set temperature, ammonia was introduced (128 sccm), then methyl acrylate was introduced (0.077 mL min$^{-1}$). For collection, the effluent gas from the FTIR flowed into a knock-out pot chilled to 5 to 10° C., packed with 6 mm soda lime glass beads, and containing a solution of 100 ppm 4-hydroxy TEMPO in 400 mL DMF.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:
1. A method comprising:
reacting a monomer having the structure

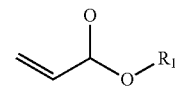

with ammonia to form a mixture comprising acrylonitrile, an alcohol, and water; and
polymerizing the acrylonitrile with at least a portion of the monomer remaining in the mixture to form a copolymer having the structure

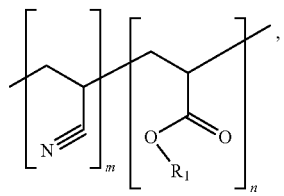

wherein:
$R_1$ comprises at least one of a first aliphatic group or hydrogen,
$100 \leq m \leq 4000$, and
$1 \leq n \leq 4000$.

2. The method of claim 1, wherein the mixture is an emulsion.

3. The method of claim 1, wherein the copolymer comprises

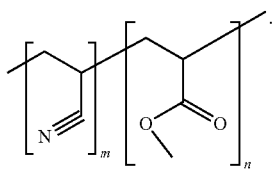

4. The method of claim 1, wherein the copolymer contains randomly dispersed repeat units derived from the acrylonitrile and randomly dispersed repeat units derived from the monomer.

5. The method of claim 3, wherein the copolymer has a molecular weight between about 5.4 kDa and about 600 kDa.

6. The method of claim 1, wherein the mixture further comprises a surfactant.

7. The method of claim 1, wherein the mixture further comprises a chain transfer agent (CTA).

8. The method of claim 1, wherein the copolymer has a peak temperature between about 200° C. and about 400° C., as determined by differential scanning calorimetry.

9. The method of claim 1, wherein the polymerizing is performed at a temperature between about 25° C. and about 100° C.

10. The method of claim 1, wherein the copolymer has an end group comprising at least one of an alkyl group or an alkoxy group.

11. The method of claim 1, further comprising converting the copolymer to a carbon fiber.

12. The method of claim 3, wherein the copolymer comprises a molar ratio of a repeat unit derived from the acrylonitrile (AN) to a repeat unit derived from the monomer (M) between about 96:4 and about 97:3.

* * * * *